US009669111B2

United States Patent
Schnabelrauch et al.

(10) Patent No.: US 9,669,111 B2
(45) Date of Patent: Jun. 6, 2017

(54) DEVICE FOR THE DIAGNOSIS OF INFLAMMATORY TISSUES IN DENTAL APPLICATIONS

(71) Applicant: THOMMEN MEDICAL AG, Grenchen (CH)

(72) Inventors: Matthias Schnabelrauch, Jena (DE); Lorenz Meinel, Wuerzburg (DE); Falko Schlottig, Fuellinsdorf (DE); Ralf Wyrwa, Rothenstein (DE)

(73) Assignee: THOMMEN MEDICAL AG, Grenchen (CH)

( * ) Notice: Subject to any disclaimer, the term of this patent is extended or adjusted under 35 U.S.C. 154(b) by 0 days.

(21) Appl. No.: 14/383,843

(22) PCT Filed: Mar. 7, 2013

(86) PCT No.: PCT/EP2013/054569
§ 371 (c)(1),
(2) Date: Sep. 8, 2014

(87) PCT Pub. No.: WO2013/131993
PCT Pub. Date: Sep. 12, 2013

(65) Prior Publication Data
US 2015/0017101 A1 Jan. 15, 2015

(30) Foreign Application Priority Data
Mar. 8, 2012 (CH) .......................... 329/12

(51) Int. Cl.
*A61K 49/00* (2006.01)
*C12Q 1/04* (2006.01)
(Continued)

(52) U.S. Cl.
CPC ............ *A61K 49/0004* (2013.01); *A23G 4/14* (2013.01); *A61B 5/14546* (2013.01);
(Continued)

(58) Field of Classification Search
CPC ... A23G 4/06; A23G 4/14; A23G 4/20; A61C 2201/00; A61C 2201/002; A61K 6/002;
(Continued)

(56) References Cited

U.S. PATENT DOCUMENTS

| 5,770,691 A * | 6/1998 | Fields | C07K 7/06 424/49 |
|---|---|---|---|
| 2001/0012636 A1* | 8/2001 | Azar | A23G 4/06 436/163 |

(Continued)

FOREIGN PATENT DOCUMENTS

| DE | 37 00 180 A1 | 7/1988 |
|---|---|---|
| WO | 01/14875 A1 | 3/2001 |
| WO | 2007/133721 A2 | 11/2007 |

OTHER PUBLICATIONS

Harald Tschesche, "Bimolecular interaction of matrix metalloproteinases and their inhibitors timps", Journal of Protein Chemistry, 1998, pp. 549-551, vol. 17, No. 6.
(Continued)

*Primary Examiner* — Jeffrey E Russel
(74) *Attorney, Agent, or Firm* — Sughrue Mion, PLLC

(57) ABSTRACT

The document proposes a diagnostic chewing gum for identifying the presence of inflammatory tissues in the mouth, in particular in or adjacent to the mandible, the maxilla, an implant or the teeth of a user, comprising a base material or particles (3) embedded and/or attached to the base material; an element (1, 5-7), like e.g. a releasable flavor molecule, attached to the base material and/or the particles, for the generation of a change in the chewing gum directly detectable by the user; wherein the element (1, 5-7) generates the change upon direct or indirect contact with a marker (4), e.g. a proteolytic enzyme, which is released by inflammatory tissue in response to bacterial mediators.

36 Claims, 2 Drawing Sheets

(51) Int. Cl.
*C12Q 1/37* (2006.01)
*G01N 33/52* (2006.01)
*G01N 33/68* (2006.01)
*A23G 4/14* (2006.01)
*A61C 19/04* (2006.01)
*A61B 5/145* (2006.01)
*A61B 5/00* (2006.01)
*A61K 9/68* (2006.01)

(52) U.S. Cl.
CPC ............ *A61B 5/4552* (2013.01); *A61C 19/04* (2013.01); *A61K 9/0058* (2013.01); *A61K 49/0069* (2013.01); *C12Q 1/04* (2013.01); *C12Q 1/37* (2013.01); *G01N 33/528* (2013.01); *G01N 33/68* (2013.01); *G01N 33/6893* (2013.01); *A61C 2201/00* (2013.01); *A61C 2201/002* (2013.01); *C12Q 2304/00* (2013.01); *G01N 2333/96494* (2013.01)

(58) Field of Classification Search
CPC .............. A61K 9/0058; A61K 49/0004; A61K 2123/00; C12Q 1/04; C12Q 1/37; C12Q 2304/00; G01N 33/528; G01N 33/68; G01N 33/6893; G01N 2333/96494
See application file for complete search history.

(56) References Cited

U.S. PATENT DOCUMENTS

2002/0034475 A1* 3/2002 Ribi ........................ A23L 1/275
424/9.6
2006/0275216 A1 12/2006 Lauffer et al.
2011/0081673 A1 4/2011 Chandsawangbhuwana et al.

OTHER PUBLICATIONS

P. Pozo, et al., "Longitudinal analysis of metalloproteinases, tissues inhibitors of metalloproteinases and clinical parameters in gingival crevicular fluid from periodontitis-affected patients", Journal of Periodontal Research, Jun. 1, 2005, pp. 199-207, vol. 40, No. 3

Ulvi Kahraman Gursoy, et al., "Use of host- and bacteria-derived salivary markers in detection of periodontitis: A cumulative approach", Disease Markers, 2011, pp. 299-305, vol. 30, No. 6.

Barnett Alfant, et al., "Matrix Metalloproteinase Levels in Children With Aggressive Periodontitis", Journal of Periodontology, May 2008, pp. 819-826, vol. 79, No. 5.

Figueredo CMS, et al., "The short-term effectiveness of non-surgical treatment in reducing protease activity in gingival crevicular fluid from chronic periodontitis patients", Journal of Clinical Periodontology, Aug. 1, 2004, pp. 615-619, vol. 31, No. 8.

Hideaki Nagase, et al., "Human Matrix Metalloproteinase Specificity Studies Using Collagen Sequence-Based Synthetic Peptides", Biopolymers (Peptide Science), 1996, pp. 399-416, vol. 40.

Masaharu Kamo, et al., "Short Communications", Journal of Protein Chemistry, 1998, pp. 505-567, vol. 17, No. 6.

International Search Report for PCT/EP2013/054569 dated Sep. 2, 2013 [PCT/ISA/210].

* cited by examiner

DEVICE FOR THE DIAGNOSIS OF INFLAMMATORY TISSUES IN DENTAL APPLICATIONS

CROSS REFERENCE TO RELATED APPLICATIONS

This application is a National Stage of International Application No. PCT/EP2013/054569 filed Mar. 7, 2013, claiming priority based on Swiss Patent Application No. 00329/12 filed Mar. 8, 2012, the contents of all of which are incorporated herein by reference in their entirety.

TECHNICAL FIELD

The present invention relates to device, in particular to a chewing gum, for the diagnosis of inflammatory tissues in dental applications.

PRIOR ART

A recent consensus meeting has concluded that peri-implantitis occurs around 12-40% of implanted teeth. This renders peri-implantitis a true threat in today's advancement of implant reliability and performance.

Arguably, the state of the art for diagnosing peri-implant infection and peri-implantitis (most advanced stage of infectious peri-implant complications) followed by most practitioners is bleeding on probing (BOP). The underlying assumption is that bleeding on probing is indicative for inflammation and advanced tissue degradation and, therefore, seen by many as indicative for peri-implantitis in the context of implants. This view is too simplistic. It has been demonstrated that only repeatedly observed absence of bleeding has a high negative predictive value (98%; i.e. the tooth and surrounding tissue are healthy) while presence of bleeding was not prognostic (positive prediction 6%; i.e. useless for prediction of disease state of teeth and surrounding tissue).

Novel tests are available, allowing point of care (PoC) assessment of collagenase expression, including systems such as MMP-8. It has been established, that MMP-8 detected within sulcus fluid is predictive to stratify healthy subjects from patients with inflammatory tissues, i.e. a high prognostic power has been demonstrated for MMP-8. Furthermore, MMP-8 levels return to normal following successful medical intervention, allowing monitoring of therapeutic success within two weeks after treatment had commenced and within the specific context of implant inflammation.

The point of care or PoC technology of measuring MMP-8 levels from sulcus fluid is complex. A test stripe, soaked with sulcus fluid collected by the dentist from the site of interest, is transferred into a complex device within which an ELISA like reaction is facilitated leading to a read-out on MMP-8 activity—in essence, a complex, expensive and difficult to handle system.

There are quite a number of scientific articles dealing with the presence and the levels of metalloproteinase activity as a function of the degree of inflammation of tissue in the mouth. Reference is for example made to Tschesche, Journal of protein chemistry 17 (6) 41, 1998, 549-551; Pozo et al in Journal of periodontal research 40 (3), 2005, 199-207; Kahrmaran et al in Disease markers, 30 (6), 2011, 299-305 as well as Barnett et al in Journal of periodontology, 79 (5), 2008, 819-826.

WO-A-2007/133721 provides a method of alleviating a sign or symptom of periodontal disease in a subject, by administering to the subject a composition containing a natural compound which inhibits matrix metalloproteinase activity and interleukin-1 activity.

SUMMARY OF THE INVENTION

It is therefore an object of the present invention to provide a new approach for the detection of inflammatory tissue in the dental field.

This and other objects are achieved by the claimed subject matter.

Specifically the present invention in particular relates to a diagnostic chewing gum for identifying the presence of inflammatory tissues in the mouth, in particular in or adjacent to the mandible, the maxilla, an implant or the teeth of a user. In accordance with the present invention, this chewing gum comprises at least one base material or particles embedded and/or attached to said base material; at least one element, such as for example a molecule, for the generation of a change in the chewing gum directly detectable (i.e. without additional analytical tools or the like so basically by using at least one of the five senses, i.e. sight—ophthalmoception, hearing—audioception, taste—gustaoception, smell—olfacoception, and touch—tactioception, or a combination thereof) by the user. In accordance with the invention, the element generates the change upon direct or indirect contact with a marker which is released by inflammatory tissue in response to bacterial mediators.

Medical uses of chewing gums as such are known. E.g. DE 3700180 provides a chewing gum which apart from acting as a conventional chewing gum allows to take up the saliva of the user like a sponge such that after taking out the chewing gum it can be analysed for example in terms of the DNA of the user. It is also proposed to have a colourant indicator in the chewing gum. However the chewing gum for analytic purposes and for the actual diagnosis needs to be taken out of the mouth of the user. US 2011/008 1673 also relates to a chewing gum for diagnostic purposes, in this case in the context of diabetes. Here the chewing gum is provided with an enzyme, e.g. horseradish peroxidase, and depending on the glucose present in the saliva of the user the chewing gum changes colour, and after taking out the chewing gum this can be compared to a colour chart to determine the risk of diabetes. WO 01/14875 also relates to a chewing gum, here for the detection of the pH value in the saliva of the user. A corresponding pH sensitive substance is dispersed in the gum base which changes colour as a function of the pH. None of these applications however relate to the detection of inflammatory tissues in the mouth or suggest such a use. In contrast, the proposed systems here allow for patient self-monitoring. The chain in this proposal is as follows: In response to tissue degradation, (i) a change for example in the form of a strong bitter taste is released by the system and (ii) this bitter taste can be reported by the patient. (iii) Based on this report, a diagnose can be made and (iv) can lead early on therapy if appropriate.

As pointed out above, peri-implantitis is a true threat in today's advancement of implant reliability and performance. The proposal is addressing this challenge by deploying the human senses, in particular for example the taste/gustatory system, for surveillance of connective tissue degradation, which marks the borderline between gingivitis/mucositis and periodontitis (also called pyorrhea, parodontitis or paradontitis)/peri-implantitis (see also FIG. 1). This radically new and easy to use diagnostic tool, identifies and stratifies subjects at risk for development of peri-implantitis, opening a new window of opportunity for medical risk assessment and, therefore, possible intervention at an early stage. This early on detection allows pre-emptive, successful, non-complex and well tolerated treatment. The strategy followed here is disruptive in terms of shifting current point-of-care (PoC; i.e. the practitioner's office) diagnosis to self-monitoring, allowing consultation of one's dentist in diseases stages which are clinically unapparent and within which relatively moderate therapeutic intervention suffice to prevent further destruction of the implant and surrounding tissues and in contrast to more radical interventions necessary at later stages (see also FIG. 1).

A completely new diagnosing platform has thus been developed by means of gaining access to the advanced technological capabilities of several contributors.

The disease course of peri-implant infection and its most severe form, peri-implantitis, commences from microbial challenge and biofilm formation. The microbial challenge triggers a defensive host response (release of cytokines and other signals) in response to bacterial mediators e.g. lipopolysaccharides (LPS; component of the cell wall of gram-bacteria), leading to massive infiltration of macrophages (Φ). It is these Φ which are capable of releasing various proteolytic enzymes, including MMPs. Among many other MMPs tested, MMP-8—also known as type II collagenase—has demonstrated impressive prognostic power to predict clinical progression through enhanced pocket formation, attachment loss, bone resorption, gingival recessions, increased tooth/dental implant mobility and finally tooth/dental implant loss. MMP-8 is disrupting the dense tissue collagen network thereby allowing efficient Φ infiltration as a prerequisite for bacteria removal—in other words, MMP-8 activity is directly linked to the first and clinically fully reversible stage of gingival connective tissue destruction (see also FIG. 1, second and third boxes from top). MMP-8 upregulation in peri-implant infection is massive as compared to other inflammatory dental disease. For example, MMP-8 levels in sulcus fluid aspirates from healthy sites arbitrarily set to 1 U (pocket depth 3.3 mm; gingival index (GI) 0.6), were elevated in moderate chronic periodontitis to 80 U (pocket depth 5.6 mm; GI 1.6) and 78 U for severe chronic periodontitis (pocket depth 5.9 mm; GI 2.0). In contrast, MMP-8 was upregulated to more than 950 U in patients with peri-implantitis (pocket depth 5.0 mm; GI 2.0) compared to healthy implants (pocket depth 2.4 mm; GI 1.0). Therefore, MMP-8 is an ultra-sensitive, prognostic biomarker for sensing peri-implant infection long before more severe disease states are attained, such as peri-implantitis. The challenge addressed in this proposal is to enable the patient for self-monitoring of MMP-8 activity using the system (conceptually presented in FIG. 1) and functionality as outlined in FIG. 2.

According to a preferred embodiment of the present invention therefore, the marker inducing the change is a proteolytic enzyme released or upregulated by inflammatory tissue, preferably by macrophages.

The marker inducing the change in accordance with yet another preferred embodiment is most preferably matrix metalloproteinase (MMP), which is preferably activated. Preferably matrix metalloproteinase-8 (MMP-8) activated matrix metalloproteinase-8 (aMMP-8), matrix metalloproteinase-2 (MMP-2), activated matrix metalloproteinase-2 (aMMP-2), matrix metalloproteinase-9 (MMP-9), activated matrix metalloproteinase-9 (aMMP-9), or a combination thereof is the maker of interest triggering the change perceivable the user of the chewing gum.

The gustatory system principally has four primary taste submodalities recognizing sweet, sour, salty, and bitter. Maximal sensitivity is provided for bitter taste and bitter taste can be calibrated for control of inter-patient variability using methods outlined in the European Pharmacopoeia. Sweet taste is more difficult to calibrate among patients but used as a strategy as well in spite of potential challenges for individual calibration of sweet perception. The human tongue offers a fascinating range of sensitivity for tasting sweetness and bitterness, covering five orders of magnitude. Quinine sulfate (bitter) is sensed down to 0.0004 mM, rivaling even our most advanced analytical detectors available today. The artificial sweetener, saccharin, is recognized down to 0.02 mM by the average human. Within the context of this application it is important, that certain short peptides can be typically sensed down 0.05 to 6 mM and this insight is deployed by designing peptide sequences for the system which result in bitter taste following cleavage. By this strategy, the coupling of a flavoring substance can be avoided as the cleaved peptide sequence itself mediates a bitter sensation recognized by the affected patient.

In conclusion, in particular the MMP-8 (System 1) protease sensitive system provides the necessary power to the dentist for early detection and continuous surveillance of peri-implant diseases. The MMP-8 sensitive system recognizes early connective tissue damage. The system provides radically new, easy to use tools to the dentist and patient for early on monitoring of peri-implant diseases with immediate relevance on patient oral health.

The proposed system aims at broad application, including sensing of oral and mucosal alterations following the principle outlined here within for peri-implant infection.

The system is thus radically shifting monitoring of peri-implant infection from assessments involving complex machinery to self-monitoring using the human tongue or the human eye of the user as a sensitive detector. Instead of restricting the monitoring of the oral health status to visits at the dentist, the approach supports frequent self-monitoring such that in case of positive signal, the subject can visit the dentist's office to get a thorough diagnosis. The system (see also FIG. 2) is the mode by which clinically unapparent oral diseased tissue becomes detected early on. The main innovation aspects are the following:

The deployment of human taste sensing/gustatory system for monitoring of inflammatory or other diseases is radically new.

Connective-tissue damage sensing dental implant system providing a perceivable response for monitoring of earliest signs of peri-implant disease have not been described.

Chewing gums with diagnostic features are known but not those which respond to the upregulation of an activated enzyme prognostic for the development of oral diseases.

Selection of MMP-8 sensitive systems from known sequences which provide the necessary performance to preferentially sense MMP-8 over other proteases in peri-implant disease.

The correlation of peri-implant disease with MMP-8 elevation as done here controls the information available in literature by data sets to provide a reliable basis for fine-tuning and adapting our system's sensitivity and selectivity to a targeted disease state of the peri-implant zone.

Modern coupling techniques are deployed to decorate the plastic (spheric system) surfaces or the gum directly with the peptide sequences.

The coupled flavoring substances may reduce their potential for (bitter) taste once attached to the peptide sequence. This risk can be mitigated by selecting different coupling sites at the (bitter) tasting molecule, by selecting different (bitter) tasting molecules and by designing bitter tasting peptide sequences, which are known to induce a bitter taste. Correspondingly therefore in accordance with yet another preferred embodiment the element can on the one hand be a molecule or molecular assembly which, upon direct or indirect contact with the marker undergoes a color change perceivable by the naked eye of the user, and which is embedded or attached to the base material or to particles embedded and/or attached to said base material.

On the other hand the element can be a flavor molecule releasably, preferably releasably covalently, attached to the base material or to particles embedded and/or attached to said base material.

The flavor molecule can be (releasably) attached to the base material or to particles embedded and/or attached to said base material by means of a hydrogen bonding or by means of a molecular chain cleavable under direct or indirect contact with the marker Release is for example possible by lysis of the molecular chain by the marker itself, it is however also possible by means of mechanisms such as agglomeration or attachment of the marker to the linker or another element close by, inducement of a conformational change or the like, corresponding reduction of the binding constant of the flavor molecule to the support and release of the molecule to generate the corresponding taste sensation.

The molecular chain can for example be a polypeptide chain or a sugar chain or a combination thereof. In case of a polypeptide chain, this is preferably constituted of 2-15, most preferably of 3-7 amino acids, and preferably the linker molecule is either directly or indirectly, via an anchoring element, attached to the base material or to particles embedded and/or attached to said base material.

Possible linker sequences to be used as molecular chain cleavable under direct or indirect contact with the marker for the attachment of e.g. a bitter flavor molecule such as quinine, caffeine, theobromine, naringin, sucralose or neotame are given by the following systems, where in those sequences which follow that contain slash marks, the slash marks indicate cleavage sites by the MMP-8 system:

```
                                                    (SEQ-ID 1)
Gly-Pro-Gln-Gly/Ile-Ala-Gly-Gln;

(SEQ-ID 2)
Gly-Asn-Gln-Gly/Ile-Ala-Gly-Gln;

(SEQ-ID 3)
Gly-Leu-Gln-Gly/Ile-Ala-Gly-Gln;

(SEQ-ID 4)
Gly-Pro-Asp-Gly/Ile-Ala-Gly-Gln;

(SEQ-ID 5)
Gly-Pro-Leu-Gly/Ile-Ala-Gly-Gln;

(SEQ-ID 6)
Gly-Pro-Gln-Glu/Ile-Ala-Gly-Gln;

(SEQ-ID 7)
Gly-Pro-Gln-Phe/Ile-Ala-Gly-Gln;

(SEQ-ID 8)
Gly-Pro-Gln-Arg/Ile-Ala-Gly-Gln;

(SEQ-ID 9)
Gly-Pro-Gln-Gly/Leu-Ala-Gly-Gln;
```

```
                                                    (SEQ-ID 10)
Gly-Pro-Gln-Gly/Tyr-Ala-Gly-Gln;

(SEQ-ID 11)
Gly-Pro-Gln-Gly/Ile-Phe-Gly-Gln;

(SEQ-ID 12)
Gly-Pro-Gln-Gly/Ile-Glu-Gly-Gln;

(SEQ-ID 13)
Ala-Ser-Gln-Lys-Arg-Pro-Ser-Gln-Arg-His-Gly-
Ser-Lys-Tyr/Leu-Ala-Thr-Ala-Ser;

(SEQ-ID 14)
Ala-Ser-Gln-Lys-Arg-Pro-Gln-Arg-Ser-Lys-Tyr/
Leu-Ala-Thr-Ala-Ser;

(SEQ-ID 15)
Ac-Pro-Leu-Gly-(2-mercapto-4-methyl-pentanoly)-
Leu-Gly-OEt;

(SEQ-ID 17)
Ac-Pro-Leu-Gly-S-CH2CH(CH3)CH2CH3;

(SEQ-ID 18)
Ac-Pro-Leu-Gly-Leu-Leu-Gly-OC2H5;

(SEQ-ID 19)
DNP-Pro-Leu-Gly-Ile-Ala-Gly-Gln-D-Arg-OH;

(SEQ-ID 20)
Lys-Pro-Leu-Gly-Leu-Lys(Dnp)-Ala-Arg-NH2;

(SEQ-ID 21)
(Gly-Pro-Hyp)5-Gly-Pro-Lys-Gly-Pro-Gln-Gly/Leu-
Arg-Gly-Gln-Lys(Dnp)-Gly-Val-Arg-(Gly-Pro-Hyp)
5-NH2;

(SEQ-ID 22)
(Gly-Pro-Hyp)5-Gly-Pro-Ser-Gly-Ala-Glu-Gly-Pro-
Lys(-Gly-Pro-Gln-Gly/Leu-Arg-Gly-Gln-Lys(Dnp)-
Gly-Val-Arg-(Gly-Pro-Hyp)5-NH2;

(SEQ-ID 23)
(Gly-Pro-Hyp)4-Gly-Pro-Lys-Gly-Pro-Gln-Gly/Leu-
Arg-Gly-Gln-Lys(Dnp)-Gly-Val-Arg-Gly-Leu-Hyp-
Gly-Gln-Arg-Gly-Glu-Arg-(Gly-Pro-Hyp)4-NH2.
```

The flavor molecule upon release preferably triggers the gustatory system of the user, preferably by stimulating a sweet and/or bitter taste.

The flavor molecule together with the linker can be a peptide itself, so e.g. one of a combination of the following systems, where the part right of the slash, if released, provides for the gustatory sensation:

```
                                                    (SEQ-ID 24)
Gly-Thr-Pro-Gly-Pro-Gln-Gly/Ile-Ala-Gly-Gln-Arg;

(SEQ-ID 25)
Gly-Thr-Ala-Gly-Pro-Pro/Gly-Thr-Pro-Gly-Pro-
Gln-Gly;
```

Generally speaking the following bitter sequences can be combined with the above mentioned linker peptides, taking the part left of the slash thereof only:

```
                                                    ((SEQ-ID 26)
    . . . /Ile-Ala-Met-Glu-Lys;

(SEQ-ID 27)
    . . . /Leu-Leu-Gly-Ala-Ile-Leu;

(SEQ-ID 28)
    . . . /Ile-Ala-Gly-Ile-Phe-Pro;
```

-continued

```
. . . /Ile-Ala-Phe-Pro;                      (SEQ-ID 29)

. . . /Ile-Ala-Gly-Ile;                      (SEQ-ID 30)

. . . /Ile-Phe-Phe-Pro;                      (SEQ-ID 31)

. . . /Ile-Phe-Ile-Phe;                      (SEQ-ID 32)

. . . /Ile-Phe-Val-Leu;                      (SEQ-ID 33)

. . . /Ile-Phe-Trp-Ile;                      (SEQ-ID 34)

. . . /Ile-Phe-Trp-Tyr;                      (SEQ-ID 35)

. . . /Tyr-Ile-Phe-Pro-Leu-Val;              (SEQ-ID 36)

. . . /Ile-Trp-Gly-Gln;                      (SEQ-ID 37)

. . . /Ile-Trp-Ile-Phe;                      (SEQ-ID 38)

. . . /Ile-Trp-Gly-Pro;                      (SEQ-ID 39)

. . . /Ile-Ala-Gly-Gln-Ile-Tyr-Pro-Ile;      (SEQ-ID 40)

. . . /Ile-Ser-Pro-Pro-Pro-Gly;              (SEQ-ID 41)

. . . /Ile-Ala-Gly-Gln-Val-Val-Val;          (SEQ-ID 42)

. . . /Gly-Pro-Phe-Pro-Val-Ile;              (SEQ-ID 43)

. . . /Phe-Ala-Leu-Pro-Glu-Tyr-Leu-Lys;      (SEQ-ID 44)

. . . /Leu-Ile-Tyr-Pro-Ile;                  (SEQ-ID 45)
```

Ethylation or acetylation just ahead of the cleavage site can be used to reduce the bitterness. E.g.:

```
OEt-Gly-Pro-Leu-Gly/ . . . ;                 (SEQ-ID 46)

CH3(O)C-Gly-Pro-Leu-Gly/ . . . .             (SEQ-ID 16)
```

Generally speaking, combinations of Tyr, Ile, Tyr, Phe, Pro, Leu, Val as well as combinations of Tyr, Ile, Tyr, Phe, Pro, Leu, Val can be used for the bitter part sequences. The change upon direct or indirect contact with the marker is, in accordance with yet another preferred embodiment, triggered when a minimum marker concentration in saliva of the user is reached. Preferably the change upon direct or indirect contact with the marker is triggered when a minimum matrix metalloproteinase marker concentration in saliva of the user is reached, in particular matrix metalloproteinase-8 (MMP-8) or activated matrix metalloproteinase-8 (aMMP-8), said minimum marker concentration in saliva for the generation of a change in the chewing gum directly detectable by the user being above 1 ng/ml, preferably above 5 ng/ml, more preferably above 8 ng/ml.

The change upon direct or in direct contact with the marker is preferably triggered when a minimum marker concentration in saliva of the user is reached, wherein preferably the marker is matrix metalloproteinase, in particular matrix metalloproteinase-8 (MMP-8) or activated matrix metalloproteinase-8 (aMMP-8), and wherein the minimum marker concentration in saliva for the generation of a change in the chewing gum directly detectable by the user is in the range of 1-6000 ng/ml, preferably in the range of 5-4000 ng/ml, and most preferably in the range of 8-2000 ng/ml.

The minimum marker concentration for the detection of periodontitis is typically a factor of 10, preferably a factor of 100, and more preferably a factor of 500 smaller than the minimum marker concentration for the detection of peri-implantitis, and wherein even more preferably based on this critical concentration difference the generation of a change in the chewing gum directly detectable by the user is differentiated between periodontitis and peri-implantitis.

The element can be attached to a particle with a size in the range of 5-300 μm, preferably in the range of 20-250 μm, wherein preferably the particle is based on a polymer or copolymer or a (co)polymer mixture or (co)polymer blend, preferably on a polymer or copolymer selected from the group consisting of polystyrene, poly(methylmethacrylate), also possible are polyethylene, polypropylene, poly(vinylchloride), polycarbonate, polyamide, polysulfone, poly(ethersulfone), polyether, poly(ether-ketone), poly(ether-ether-ketone), poly(tetrafluoroethylene), poly(vinylidenefluoride), polyester, poly(hydroxyalkanoate), polyurethane, polyimide, poly(ether-imide), poly(butadiene), poly(vinylbutyral), polyanhydride, poly(amino acid), poly(organosiloxane), cellulose, chitin or a mixture or blend thereof. The systems can form a three-dimensional matrix, e.g. due to cross-linking processes. The three-dimensional matrix can be based on carboxy groups, amino groups, thiol groups or combinations thereof. Preferably poly(methylmethacrylate) with a threedimensional carboxy group matrix is used.

Preferably the element, or an interlinked anchoring element, is attached to the particle by means of conventional coupling techniques, preferably by disulfide coupling, by implementation of esterified bromine compounds with sodium azide or by coupling via dicarboxylic acid, diisocyanate or diepoxide. The element, or an interlinked anchoring element, can be attached to the particle by amide formation using peptide coupling methods, disulfide coupling, ester formation using procedures like carbodiimide-activated esterifications, urethane, urea or isothiourea formation generated by reaction with diisocyanates or diisothiocyanates, ether formation by reaction with epoxy group containing molecules like diepoxides or activated haloalkyl derivatives, reaction with dialdehydes followed by reductive amination, Michael-type addition reaction as e.g. performed by reaction of an acrylated reaction partner with a thiol-modified one or by known Click Chemistry coupling protocols like the Cu(I)-promoted azide-alkyne [3+2] cycloaddition. Oral and/or mucosal alterations due to inflammatory tissue normally induce the change, in particular at least one of the following inflammatory states: gingivitis, mucositis, periodontitis, peri-implantitis, or a combination thereof.

Furthermore the present invention relates to the use of a chewing gum as outlined above for the detection of inflammatory tissue in the mouth, in particular in or adjacent to the mandible, the maxilla, an implant or the teeth of a user.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings, FIG. 1 schematically shows the diagnostic approach followed in this application for early diagnosis of risk factors for the development of peri-implant infections, wherein the system (box 5) is sensing matrix metalloproteinase (MMP) regulation indicative for connective tissue degradation as present at the borderline of gingivitis/mucositis and periodontitis/peri-implantitis; today complications are typically recognized once clinical signs appear (box 4) a stage at which the disease course may be irreversible and lasting complications may prevail; today, single assessments can be done in the dentist's office using point of care systems which measure preferentially MMP-8 from sulcus fluid samples collected around the affected implant, wherein naturally, these single assessments provide limited information; the proposed systems are designed to allow on-demand, self-monitoring, so therefore the patient is providing continuous monitoring and based on this the dentist can diagnose complications early on.

DESCRIPTION OF PREFERRED EMBODIMENTS

Figure 3:
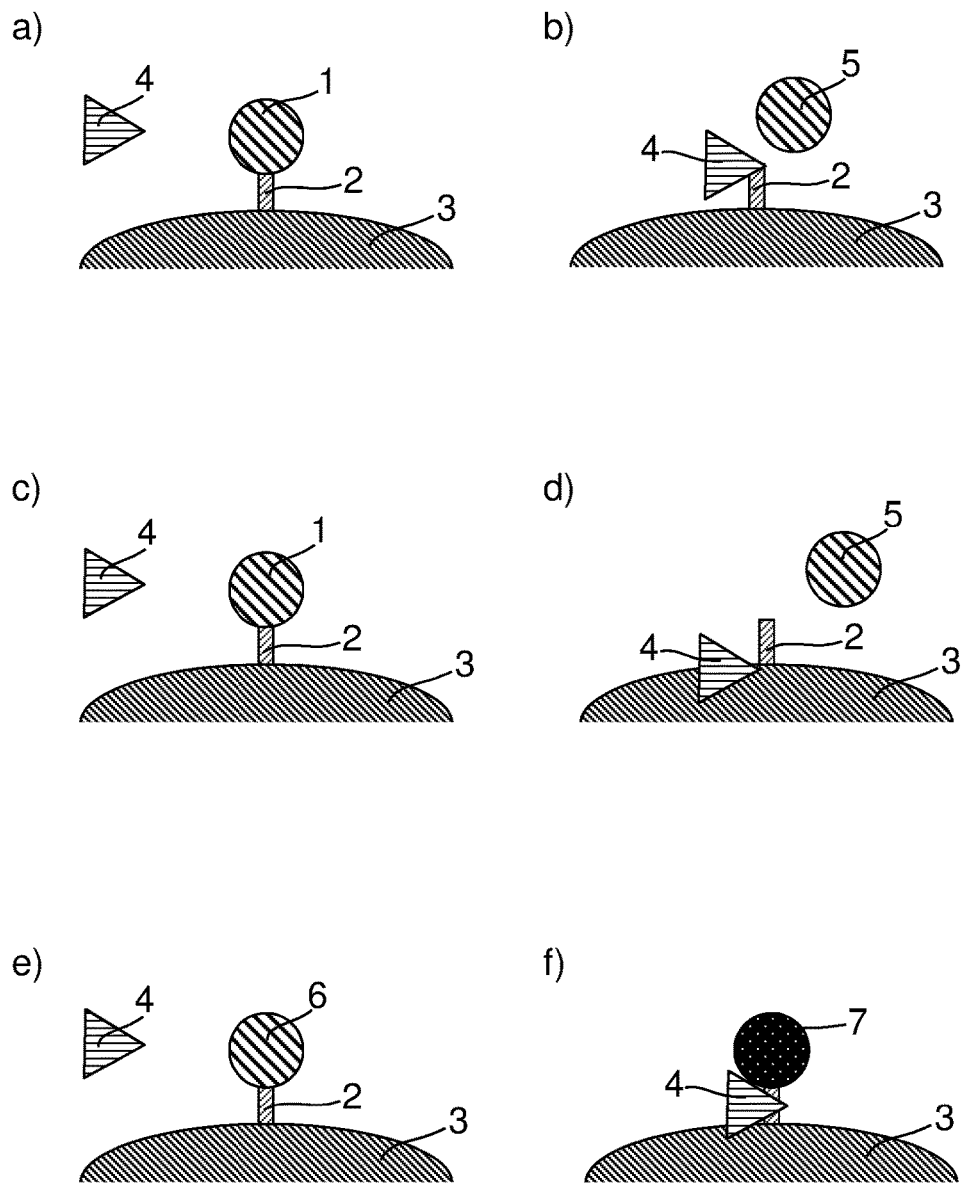
FIG. 3 shows different embodiments, wherein in a) and b) a first embodiment is shown, in which the linker sequence attached to a substrate or an anchor, to which initially (a) the flavoring substance is attached, is cleaved for the release of the flavoring substance (b), in c) and d) a second embodiment is shown, in which the linker sequence attached to a substrate or an anchor, to which initially (c) the flavoring substance is attached by a non-covalent bonding, for example a coordinative bonding, is conformationally changed such as to release the flavoring substance (d), and in e) and f) a third embodiment is shown, in which a substance attached via linker to a substrate (e) and showing a color change upon contact with the trigger molecule.

FIG. 3 shows different possibilities for attachment of releasable flavor substances 1 (a)-(d) or for the attachment of a colorant susceptible to change color upon interaction with MMP, in particular MMP-8, present in saliva.

In the first embodiment as illustrated in FIG. 3a, on a substrate 3, which can for example be a particle or the base material of the chewing gum, the flavoring substance molecule or complex 1 is attached via a linker element 2, normally a short and cleavable polypeptide chain. The flavoring substance molecule 1 may itself be a polypeptide or protein, and it may just be the extension of the linker element 2. Upon contact of the marker 4 present in saliva with the linker element 2, the latter is cleaved due to proteolytic interaction, releasing the flavoring substance into the free state 5, inducing the taste sensation (see FIG. 3b).

As illustrated in FIGS. 3c) and d), the interaction between the trigger/marker 4 present in saliva is not necessarily a direct interaction in the sense of a proteolytic interaction between the MMP trigger and the linker element, it can also be and indirect interaction for example in the sense that the MMP trigger attaches or forms a complex with the substrate in the vicinity of the linker element, induces some change, for example a change in the hydrogen bonding structure, and thereby releases the flavoring molecule or flavoring complex 5 into the surrounding saliva. In this case there is normally no chemical bond between the linker element 2 and the flavoring substance 1, however it is also possible that the MMP trigger attaches and itself triggers a proteolytic system mounted on the substrate 3 or the linker element 2 leading to a proteolytic cleavage for the release of the flavoring substance.

FIGS. 3e) and f) show the situation where the MMP trigger does not induce release of flavoring substance but a color change. To this end upon contact of the MMP trigger 4 with the corresponding colorant substance 6, the latter is transformed into a second, differently colored state 7 leading to a visual signal perceptible to the user and indicative offer a sufficient level of MMP trigger in saliva. It is not only possible that, as illustrated in FIGS. 3e) and f), the color change takes place in a situation where the colorant 6 remains to be fixed to the chewing gum, it is also possible that the colorant 6 is released upon contact with the MMP trigger leading to a color change in saliva or in mouth tissue perceivable to the user.

EXPERIMENTAL SECTION

In a first step peptide sequences composed of (i) anchor coupled to (ii) sensitive peptide sequence coupled to (iii) flavoring substance using solid phase chemistry (FIG. 2), were synthesized by using a solid phase synthesis of MMP-8 sensitive systems.

Three components of the system were synthesized (from C-N Terminus): (i) anchor coupled to (ii) sensitive peptide sequence coupled to (iii) flavoring substance.

30 systems with different protease sensitive protein sequences (as a platform from which sequences can be selected with best MMP-8 selectivity and tailored sensitivity to MMP-8 cleavage) were synthesized. Absolute MMP-8 selectivity is unlikely as proteases typically have broad substrate specificity such that systems are optimized for preferential (strict MMP-8 exclusivity is perceived impossible) MMP-8 reporting. Some cross-sensitivity of the MMP-8 responsive system and particularly to MMP-1 or MMP-3 must be tolerated and was tested. Conceptually and diagnostically, this cross-sensitivity is unproblematic, as MMP-1, MMP-3 and particularly MMP-8 are concomitantly upregulated by infiltrating Φ towards bacteria residing in host tissue, i.e. the same physiological mechanism is sensed by all three proteases. Nevertheless, a relative rate (MMP-8 cleavage over MMP-1 or MMP-8 cleavage over MMP-3) of at least 50:1 is a specification, as is e.g. the case for the sequences SEQ-IDs 2, 6 and 10. More sensitive protein sequences and their relative rate compared to MMP-1 hydrolysis are selected. Synthesis is performed on an in-house, automated solid phase peptide synthesis (SPPS) platform. Synthesis (C to N-terminus) is following established protocols by coupling the carboxyl group of one amino acid to the amino group of another and by adequate use of protecting groups to avoid unintended reactions. Finally, the flavoring substance is attached as outlined below. The taste of the cleaved peptide sequence fragment coupled to the flavoring substance was tested by human volunteers and feedback from these tests helped to further modify the peptide sequence and flavoring substance for optimized bitter taste.

Bitterness in oligopeptides is closely related to hydrophobicity. In fact and for screening purposes, one can proceed by assaying the Q value of peptides (a measure of the average hydrophobicity of a peptide, with Q>1,400 cal/mol being a threshold for possible bitter taste). Based on this approach, a selection of the following MMP-8 cleavage products suggests bitterness or not: the first five sequences (sequences #1-5) of Table 2 of NAGASE, H. & FIELDS, G. B. 1996; Human matrix metalloproteinase specificity studies using collagen sequence-based synthetic peptides. Biopolymers, 40, 399-416, show a Q* in cal/mol of approximately 1400-1700 and e.g. the fourth sequence shows bitter taste. If the cleaved peptide sequence is sufficiently bitter for reliable recognition, the coupling of the flavoring substance is sometimes not necessary.

Sequences #1-5 are a selection of MMP-8 sensitive sequences from Nagase, with #4 being predicted as bitter and #2 being predicted as not bitter based on Q value calculations. Modification of #2 by decoration with another isoleucine and/or leucine at the C-terminus leads to a prediction of bitterness and has been optimized for bitterness in terms of presenting leucine at the N- and C-terminal ends, respectively. Inconsistencies have been reported when linking Q values and bitterness, thus sensory tests are important to confirm the Q-based prediction. Typically, sensory recognition thresholds for peptides are between 0.05 and 6.0 mmol/L, i.e. less than what is sensed for quinine (about 0.0004 mmol/L). Quinine and other strong taste substances are coupled as well and as an alternative to using the bitter taste of cleaved products as given above.

Figure 1:
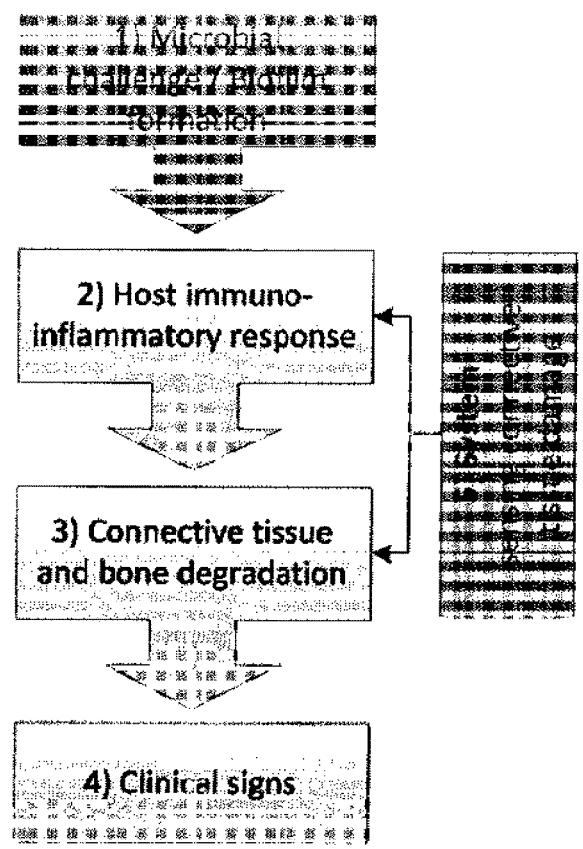
Figure 2:
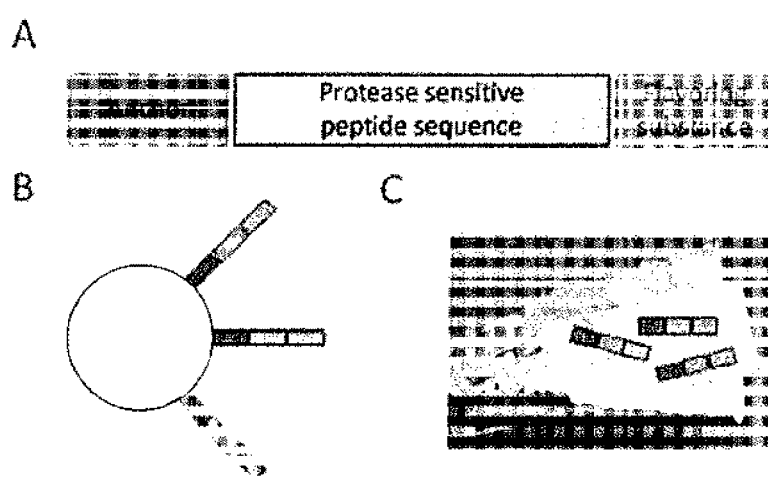
FIG. 2 shows in (A) how the functionality is linked to the MMP-8 protease sensitive peptide sequence (center portion) located in between an anchor (left) and a flavoring substance (right); in (B) how the sequence is linked to particles or another surface, referred to as 'system' in this application; upon contact with MMP-8 at specific levels, the peptide sequence is cleaved and the off-coming flavoring substance triggers an intensive taste recognized by the patient; in (C) how the system is formulated into a chewing gum; during chewing, the self-monitoring is on for connective tissue damage being a prognostic factor for developing peri-implant infection; the chewing gum is providing a full mouth profile; clearly, when activated, a dentist must perform a thorough diagnosis to identify the root cause of the positive signal as tasted by the patient.

Coupling of quinine (bitter for gustatory detection and fluorescent for easy testing of cleavage, particularly when the spherical system is deployed) or aspartame, an artificial sweetener to the N-terminal end of the 'anchor-protease sensitive peptide' sequence can be performed while still on solid phase (see FIG. 2). Bifunctional linkers can be used to couple quinine to the N-terminal end of the anchor-protease sensitive protein sequence. To avoid rapid cleavage of the linker from quinine in vivo, hydrolytically or enzymatically less sensitive linkages can be installed. In a first approach, a diisocyanate linker like hexamethylene diisocyanate is treated with the free secondary OH-group of quinine forming an urethane bond followed by coupling the linker via its remaining isocyanate group to the N-terminal end of the peptide, forming an urea bond. A second approach consists in the reaction of the quinine double bond with a bis-epoxide (e.g. 1,4-butanediol diglycidyl ether) leading to an ether linked quinine which can be subsequently coupled to solid phase attached protein by N-alkylation. Aspartame, or if necessary a N-protected aspartame, can be coupled via its carboxyl group to the peptide N-terminus by conventional peptide synthesis. After coupling the flavoring molecules to the peptide, the formed conjugates can be cleaved from solid phase, purified and characterized using common analytical methods (FT-TR, NMR, MS). The strategy regarding the anchor is outlined below.

Formulation of a spherical system in a chewing gum.

To prepare peptide-flavoring substance conjugate-bearing spheres, poly(methylmethacrylate) (PMMA) carriers (particle diameter: 17 to 30 μm) with a three-dimensional carboxy group matrix are used. The conjugates synthesized as outlined above are immobilized to the PMMA spheres by conventional peptide formation protocols (e.g. by using water-soluble carbodiimides to activate the carboxyl groups of the PMMA matrix). In cases where conjugates with interfering functional groups are used the disulfide coupling method can be employed as described above.

For the coupling of peptides to build up the sensitive peptide sequence the following method was used:

Manual Coupling of Amino Acids: After swelling the resin for 30 min in DMF and removing 1 mL 40% piperidine/DMF is added and incubated for 3 min. Then, after removing by vacuum filtration 1 mL 20% piperidine/DMF is added and incubated for 10 min. After removing the resin is washed 6 times with DMF (1 mL, 1 min each). The amino acid (5 eq) is dissolved in 410.90 μL 0.5 M HOBt in DMF and afterwards transferred to the N-terminal-deprotected peptidyl resin. 31.81 μL (8 eq) of DIC is added to the reaction mixture and gently shaked for 1 h. After removing the reaction mixture by vacuum filtration the resin is washed 6 times with DMF (1 mL, 1 min each) and 6 times with DCM (1 mL, 1 min each). After the cleavage of peptides by using MMP. The monoisotopic masses have to be checked with MALDI-MS. Preparative purification by high-pressure liquid chromatography (HPLC) is carried with a Phenomenex C18 column (21.2-mm internal diameter, 250-mm length, 7-mm particle size) with eluent A (0.2% TFA in water) and eluent B (0.2% TFA in 1:4 water-acetonitrile). The peptides have to be purified with a gradient of 29 to 54% eluent B in 50 min. For the coupling of the flavoring substance (quinine, caffeine, theobromine, naringin, sucralose or neotame) to the sensitive peptide sequence the following specific methods can be used:

Modification of hydroxygroup-containing flavor molecules with anchor groups:

Example 1

1.5 mmol of the flavor molecule is dissolved in dichloromethane and consecutively 3 mmol of adipic acid, 3 mmol of N,N-dicyclohexylcarbodiimide and 3 mmol of 4-(N,N-dimethylamino)pyridine are added. The mixture is stirred for 24 hours at room temperature. Then, the reaction mixture is washed thoroughly with saturated NaHCO3 solution, 2N HCl solution and water. The organic phase is isolated, dried over MgSO4, and evaporated to dryness under vacuum. The obtained raw material is purified by flash chromatography using a silica gel column and chloroform/methanol as eluent.

Example 2

3 mmol dodecanedioic acid are stirred at room temperature with 3 mmol of 2,4,6-trichlorobenzoyl chloride and 10 mmol of triethylamine in toluene. After 3 hours stirring, 3 mmol of quinine and 3 mmol of 4-(N,N-dimethylamino) pyridine are added and the mixture is stirred for another 20 hours. The reaction mixture is washed thoroughly with saturated NaHCO3 solution, and water, and the aqueous phase is washed twice with ethyl acetate. The organic phases are unified and dried over MgSO4. After evaporation of the solvent under vacuum, the obtained raw material is purified by flash chromatography using a silica gel column and chloroform:methanol=3:1 as eluent. Yield: 47%, brown oil. IR (ATR, cm-1): 2923, 2852, 1738, 1623, 1590, 1505, 1476, 1433, 1357, 1305, 1229, 1157, 1090, 1033, 995, 914, 852, 829, 762, 719.

Example 3

Step 1: A mixture of 1 mmol of quinine, 1 mmol of 11-bromo-undecanoic acid, 1 mmol of N,N-dicyclohexylcarbodiimide and 1 mmol of 4-(N,N-dimethylamino)pyridine in dry dichloromethane are stirred for 24 h at room temperature. Then, the reaction mixture is washed thoroughly with saturated NaHCO3 solution, 2N HCl solution and water. The organic phase is isolated, dried over MgSO4, and evaporated to dryness under vacuum. The product is further purified by flash chromatography using a silica gel column and methanol as eluent. Yield: 20%, yellow oil. IR (ATR, cm-1): 3323, 2924, 2852, 2119, 1738, 1695, 1619, 1571, 1509, 1452, 1357, 1310, 1223, 1167, 1086, 1029, 990, 914, 852, 833, 719, 647.

Step 2: 1 mmol of the flavor molecule containing a bromo group is dissolved in DMF and an excess of sodium azide (3 mmol) is added. The mixture is stirred for 20 h at room temperature. After addition of water the reaction mixture is extracted three times with ethyl acetate. The received raw product is further purified by flash chromatography using a silica gel column and chloroform:methanol=3:1 as eluent.

Example 4

2.5 mmol of the flavor molecule are dissolved in dichloromethane and 0.025 mmol of dibutyltin dilaurate followed by 5 mmol of hexamethylene diisocyanate dissolved in dichloromethane are added. The mixture is stirred for 24 hours at room temperature. After evaporation of the solvent the isocyanate-containing flavor molecule is used without further purification in the next step.

Example 5

2.5 mmol of the flavor molecule and 5 mmol of poly(ethylene glycol)-diepoxide (molecular weight: 2000 Da) are dissolved in DMSO (20 ml) followed by the addition of 5 mmol KOH. After stirring for 3 hours at room temperature water is added and the mixture is extracted with chloroform. The organic phase is dried over MgSO4 and after evaporation of the solvent, the resulting product is used without further purification.

Modification of peptides with anchor groups:

Example 6

1 mmol of the peptide is dissolved in a dioxane/water mixture (1:1) and 2M NaOH is added until the pH reached 9-10. Under a nitrogen atmosphere, 1.1 mmol 3-butyn-1-yl-chloroformate is added and the mixture is allowed to stir for 18 hours. The product is lyophilised and purified by FCPC using an n-BuOH/H2O system. After purification the product is obtained as a white solid.

Coupling of the carboxy group-containing flavor molecule with the peptide

Example 7

A mixture of 1 mmol of the carboxy group-containing flavor molecule from example 1 or 2, 1 mmol of the peptide, 1 mmol of N,N-dicyclohexylcarbodiimide and 1 mmol of 4-(N,N-dimethylamino)pyridine in dry dichloromethane are stirred for 24 h at room temperature. Then, the reaction mixture is washed thoroughly with saturated NaHCO3 solution, 2N HCl solution and water. The organic phase is isolated, dried over MgSO4, and evaporated to dryness under vacuum. The product is further purified using preparative HPLC.

Example 8

0.5 mmol of the triple bond containing peptide from example 6 and 0.5 mmol of the azide group-containing flavor molecule from example 3 are dissolved in 20 ml of DMF. After addition of the catalyst copper-1-bromide/pentamethyldiethylenetriamine (0.05 mmol), the mixture is stirred for 24 hours at room temperature. After addition of water (150 ml), the mixture is extracted three times with chloroform. The unified chloroform extracts are washed with saturated NaHCO3 solution, 2N HCl solution and water. The organic phase is dried over MgSO4 and after evaporation of the solvent the peptide-coupled flavor molecule is obtained as a light yellow solid.

Example 9

1 mmol of isocyanate-terminated flavor molecule is dissolved in dichloromethane (10 ml) followed by the addition of 0.005 mmol dibutyltin dilaurate. After addition of 1 mmol of the peptide the mixture is stirred for 24 hours at room temperature. The reaction mixture is diluted by adding 10 ml of dichloromethane and washed with saturated NaHCO3 solution, 2N HCl solution and water. The organic phase is dried over MgSO4 and after evaporation of the solvent, the resulting raw product is purified using preparative HPLC.

Example 10

1 mmol of the epoxide-modified flavor molecule and 1 mmol of the peptide are dissolved in DMSO (20 ml). 2 mmol KOH are added and the mixture is stirred for 6 hours at room temperature. Water is added and the reaction mixture is extracted several times with chloroform. The organic phase is washed with saturated NaHCO3 solution, 2N HCl solution and water. The chloroform extracts are dried over MgSO4 and after evaporation of the solvent under vacuum, the remaining material is purified using preparative HPLC.

For the coupling of flavor molecule-modified peptide to polymer particles the following methods can be used:

Example 13

The amino group-containing polymer particles (100 mg) are suspended in dichloromethane and a solution of 1 mmol of the peptide in dry dichloromethane is added. After 5 min of stirring, 1 mmol of N,N-dicyclohexylcarbodiimide and 1 mmol of 4-(N,N-dimethylamino)pyridine dissolved in dichloromethane are added and the mixture is stirred 24 h at room temperature. The particles are isolated and washed twice with dichloromethane, ethanol, and water.

Example 14

The amino group-containing polymer particles (100 mg) and the flavor molecule-containing peptide (1 mmol) are suspended in phosphate buffer saline (10 mg/ml, pH=5-6). After 5 min, 1 mmol 1-(3-Dimethylaminopropyl)-3-ethyl-carbodiimide hydrochloride (EDC) and 0.6 mmol of N-hydroxysuccinimide are added and the mixture is stirred for 4 hours at room temperature. The polymer particles are isolated, washed with deionized water and purified by dialysis against deionized water for 36 hours at room temperature. Suitable purification routines for the spheres have been established as well as analytical techniques to characterize them (particle size after immobilization, mechanical integrity, load capacity).

Development of a spherical system formulated in chewing gum.

The chewing gum can be selected from sorbitol, mannitol or a combination of these sugars/polyols to result in strong bite strength (low load of spherical system), medium bite strength (caramel like in the beginning, medium load of spherical system), or smooth system (high load of spherical system). This starting material is a free floating powder, allowing easy mixture with other components, including spherical systems such as from above. The average powder particle size is about 200 to 250 μm or even 200 to 340 μm such that particle segregation can sometimes be problematic for spherical systems of diameters less than 20 μm. In cases in which segregation is a problem, one can prepare a pre-mix in Mannitol DC granulate and compact that premix. The powder mixture typically requires a lubricant for compression (e.g. 1.5% Magnesium Stearate or 3% Mg-stearat: Talkum (1:1)). Compaction is done on a standard rotary tablet machine (possible advantageous Parameters:

Pressing force: 7 KN, Pre-pressure: 2.2 KN, Cylinder height (compression): 2.8 mm, Cylinder height (pre-compression): 3.5 mm, Tablet diameter: 14 mm, Tablet height: 5 mm, Tablet weight: 1.15 gr). Turnover is up to 6,000 chewing gums per hour or at nearly any scale less, allowing pilot scale manufacturing for mitigating production risks for later production of the system in chewing gum. Miniaturized systems are used, allowing rapid formulation screens with lab scale experiments (mini-tablets/chewing gums) as are single-punch tablet machines one of which is equipped with appropriate pressure monitoring systems as a prerequisite for rationale design of tabletting conditions. A typical formulation is compressed from 86.5% or 86.95% Pharma-gum® S and 0.5% or 0.05%, respectively, spherical system, 3% magnesium stearate, 7% sorbitol and 3% sodium carbonate. As an alternative three different Health in Gum® by CAFOSA powder mixtures will be used. Typical formulations contain 92.7% Health in Gum®, 0.05% spherical system, 2.0% Powder Flavor, 2.0% Encapsulated Flavor, 1.5% Lubricant, 1.0% Silicon Dioxide, 0.55% Liquid Flavor and 0.20% Intensive Sweeteners.

Stability tests are performed by exposing the spherical system/chewing gum formulation to different temperature and humidity profiles. The resulting chewing gums are chemically inert and not or only slightly hygroscopic and stable when stored. The formulations do not contain acid components such that re-agglomeration of the gum part while chewing is prevented. The resulting formulations can be further characterized in terms of compression force, excipient optimization of the formulations, stability studies, compaction density by mercury porosimeter as well as measurements of hardness, water content and other standard pharmaceutical characterization tests.

Collection of sulcus fluid from peri-implant diseased patients in different disease stages and from healthy peri-implant pockets and medical examination and determination of MMP-8 levels from samples obtained, definition of disease-stage specific threshold MMP-8 concentrations by correlation of measured MMP-8 concentrations with clinical diagnosis: Collection of sulcus fluid and MMP-8 levels:

Patients with peri-implant disease and healthy subjects carrying an implant were examined during clinic visit. After informed consent had been obtained, all subjects answered a questionnaire, followed by a radiological investigation and oral examination. The oral examination included periodontal parameters such as probing pocket depths, clinical attachment level, and recession at the index implant, as well as overall oral hygiene and bleeding index.

Sulcus fluid was collected from the index peri-implant zone using standardized MMP-8 collection strips, which are placed into the periodontal pockets for 30 seconds. The aMMP-8 was eluted from the strips for 30 seconds and quantitatively assessed with the DentoAnalyzer (Dentognostics GmbH, Jena, Germany). The DentoAnalyzer is a validated CE marked PoC machine, automatically conducting the entire assay process within 12 minutes chair-side. The assay allows assessment within a range of 2 ng/ml aMMP-8 in eluate up to 200 ng/ml aMMP-8 in eluate.

The MMP-8 concentrations in sulcus fluid were correlated with the clinical examination such that threshold values could be defined as a function of disease scoring.

Establishment of the system's MMP-8 performance (specificity and sensitivity):

For these tests, an in-house machine was engineered using a tool shop. By reference of the European Pharmacopeia (Pharm.Eur.) monograph for testing of chewing gums, the machine consists of two electronically controlled pistons transmitting twisting and pressing forces as occurring during chewing of a gum. A third vertical piston ('tongue') is holding the gum in place. The set-up is integrated into a temperature controlled chamber (40 mL volume) within which 20 mL of buffer or artificial saliva is placed. The buffer or saliva is spiked with respective proteases as outlined below for testing performance (selectivity and specificity) of the spherical system formulated into a chewing gum. Fragments occurring in the buffer or artificial saliva are analyzed by HPLC equipped with a fluorescence detector (in case of quinine decoration, which is strongly fluorescent) or by LC-MS/MS to provide higher sensitivity. The use of Pharm.Eur. monograph methods and qualified analytical method provides immediate relevance of the results for future submission of the system to Health Authorities when seeking marketing authorization.

In vitro testing of system sensitivity to MMP challenge:

The system was challenged to different MMPs and 5 systems are selected with optimized specificity and selectivity for MMP-8 cleavage.

Profile system cleavage as in FIG. 2B, D (coupled to spherical carrier or that coupled spherical carrier formulated into chewing gum) when exposed to MMPs. MMP-1, 2, 3, 7, 8, 9, 13 was purchased. Enzyme assays were conducted to determine kcat/KM values (as substrate concentration is high, the enzyme is saturated and reaction kinetics are, therefore, controlled by kcat) and relative rate for sequence specificity (MMP-1, MMP-2 and MMP-13 over MMP-8). Cleavage was assessed through conventional HPLC methods with UV-VIS detection and fluorescence detection where appropriate (fluorescence for e.g. quinine modified systems). Triple stage LC-MS/MS was used for analysis and characterization of fragments. As fragments are below 1500 amu (m/z), the LC-MS/MS deployed at UWU is capable of robustly assessing these cleavage products with high sensitivity while concomitantly collecting structural data by means of tandem mass spectrometry (MS/MS) for enhanced identification and confirmation.

Evaluation of system functionality/chewing gum in patients, performing patient acceptance assessment/gustatory sensitivity of flavoring substances:

Patients that have at least one implant that was inserted ≥1 year before study start with suspected soft tissue inflammation/peri-implantitis were used. After screening for their eligibility to participate in this study (inclusion/exclusion criteria) they were asked to sign the informed consent form (ICF). Clinical parameters i.e. modified plaque index (mPLI), modified sulcus bleeding index (mSBI), periimplant pocket depth (PPD), distance implant to sulcus margin (DIM) and clinical attachment height (CAL), as well as bleeding on probing (BoP) was assessed. A periapical X-ray was done to confirm the presence of a coronal translucency (positive X-ray). Patients with confirmed peri-implant disease (positive BoP and positive periapical X-ray) received either the peri-implant gustatory sensor in chewing gum or the corresponding "dummy" in a randomized order. Their gustatory response was recorded. Each patient was calibrated for one's own correction factor as outlined below.

Sample size: At least 20 patients, (sequential study design with each patient being blinded and receiving the gustatory sensor in chewing gum or corresponding dummy with at least 30 minutes waiting time between administrations).

Methods: Patients with clinically confirmed peri-implant inflammation (BoP; X-ray) were treated with either the "Peri-implant gustatory sensor" in chewing gum (test group; provided in chewing gum as outlined above) and corresponding "dummy" (control group; as verum group with placebo chewing gum) using a predefined randomization list and at least 30 minutes waiting time between treatments. Individual gustatory response was normalized after calibration as outlined below.

Gustatory assessment, chewing of peri-implant gustatory sensor in chewing gum: record patient gustatory experience (bitter taste/no specific taste) after calibration (individual correction factor is determined) of each patient as outlined below.

Taste testing of system:

These studies are needed to evaluate the taste of the cleaved peptide sequences carrying the flavoring substance. For that, the truncated peptide sequence representing the "cleaved" part following protease-cleavage of the system and carrying the flavoring substance (see FIG. 2A) is tested as outlined below. In principle one can proceed in two phases: Phase I is the calibration of each volunteers (determination of correction factor) and phase 2 is the exposure to the peptide fragment carrying the flavoring substance, for which bitterness values are collected as outlined below:

The anticipated flavoring substances (bitter) used in this disclosure are not from a single chemical class (e.g. peptides vs. quinine). Bitter substances typically have a ring-bound carbonyl group, which may be part of a lactone ring system with ring opening typically leading to a loss of bitter taste. For assessment of bitter taste, the reciprocal value of the dilution of the bitter substance which is barely noticed as bitter, is taken. Therefore, the bitter value 10,000 means that 1 g of the subject tested and diluted in 10,000 mL water is barely recognized as bitter. The bitter value is determined as the average of 6 single measurements which is performed by 6 volunteers. As this is a biological testing assay, each person must be calibrated before the study commences with an individual correction factor being calculated for each volunteer after calibration has been finished. For that, quinine-HCl with a bitter value of 200,000 is used (dilute 0.1 g quinine-HCI R in 100 mL water R. 1 mL of that solution is taken and diluted to 100 mL with Water R=stock solution. Different volumes of that stock solution is diluted with water R to 10 mL=reference solution). If a volunteer barely tastes this reference solution as bitter, no correction factor is required. In all other cases, a correction factor is determined as follows: Each volunteer receives the same volume of diluted quinine-HCl. If the person is barely not sensing bitterness, the volunteer must keep the solution in ones mouth for 30 seconds. Exactly 10 minutes must be waited before testing the person again with another dilution. The solution is held at room temperature and before the solution is tasted, the mouth is rinsed by the volunteer with water. During the entire procedure, it is not allowed to eat or smoke other than some unflavored white bread. The correction factor is calculated as of k=n/5 with n being the amount in milliliter of the stock solution barely tasted as bitter. Volunteers who cannot taste a reference solution composed of more than 5.8 mL stock solution diluted to 10 mL with water R are excluded from testing due to missing sensitivity. For testing of the flavoring substances/systems developed here within, the fragments generated after protease cleavage are manufactured and linked to the flavoring substance and these fragments are used for testing. For that, 10 mg of the fragment is dissolved in 1 mL of water R under agitation. After dissolution, this solution is diluted to 100 mL using water R (referred to as solution C1, which as a dilution factor of 100). 10 mL of that solution is diluted with water R to result in 100 mL of solution C2 (dilution factor 1,000) and so on. Starting as of C4, each volunteer determines ones individual bitter threshold level and barely tasted solution, respectively. This barely tasted solution is referred to as D. Using D, the following dilution set is prepared with the volumes always being filled to 10 mL using water R: 1.2, 1.5, 2.0, 3.0, 6.0, 8.0 mL. One determines the amount in mL of solution D, which is barely tasted as bitter. For each volunteer, the bitter value is calculated as follows: (Y*k)/(X*0.1), with Y being the individual dilution factor of Cn=D having been barely recognized as bitter, k being the correction factor as outlined above and X being the amount of mL of solution D, which has been recognized as bitter. The procedure is linked to an error of about 20-30%, which is respected during data interpretation.

| LIST OF REFERENCE SIGNS | |
|---|---|
| 1 | flavoring substance |
| 2 | linker element |
| 3 | substrate and/or anchor |
| 4 | MMP trigger |
| 5 | released flavoring substance |
| 6 | colorant substance in first state |
| 7 | colorant substance in second coloured state |

The invention claimed is:

1. A diagnostic chewing gum for identifying the presence of inflammatory tissues in a mouth of a user, comprising
 a base material or particles embedded, attached, or both, to said base material;
 an element attached to said base material or said particles or both for the generation of a change in the chewing gum directly detectable by the user;
 wherein the element generates the change upon direct or indirect contact with a marker which is released by inflammatory tissue in response to bacterial mediators, wherein the marker inducing the change is a proteolytic enzyme released by inflammatory tissue.

2. The chewing gum according to claim 1, wherein the marker inducing the change is a matrix metalloproteinase.

3. The diagnostic chewing gum according to claim 1, wherein the element is a flavor molecule releasably attached to the base material or to the particles embedded or attached to said base material.

4. The chewing gum according to claim 3, wherein the flavor molecule is attached to the base material or to the particles embedded or attached to said base material by means of a molecular chain cleavable under direct or indirect contact with the marker.

5. The chewing gum according to claim 4, wherein the molecular chain is a polypeptide chain, either directly or indirectly, via an anchoring element, attached to the base material or to the particles.

6. The chewing gum according to claim 3, wherein the flavor molecule upon release triggers the gustatory system of the user.

7. The chewing gum according to claim 3, wherein the flavor molecule is a polypeptide chain, either directly or indirectly, via an anchoring element, attached to the base material.

8. The chewing gum according to claim 1, wherein the change upon direct or indirect contact with the marker is triggered when a minimum marker concentration in saliva of the user is reached, and wherein the minimum marker concentration in saliva for the generation of a change in the chewing gum directly detectable by the user is above 1 ng/ml.

9. The chewing gum according to claim 1, wherein the change upon direct or indirect contact with the marker is triggered when a minimum marker concentration in saliva of the user is reached and wherein the minimum marker concentration in saliva for the generation of a change in the chewing gum directly detectable by the user is in the range of 1-6000 ng/ml.

10. The chewing gum according to claim 8, wherein the minimum marker concentration for the detection of periodontitis is a factor of 10 smaller than the minimum marker concentration for the detection of peri-implantitis.

11. The diagnostic chewing gum according to claim 1, wherein the element is attached to a particle with a size in the range of 5-300 µm.

12. The chewing gum according to claim 11, wherein the element is a molecule or molecular assembly which, upon direct or indirect contact with the marker undergoes a color change perceivable by the naked eye of the user, and which is embedded or attached to the base material or to the particles embedded or attached to said base material.

13. The chewing gum according to claim 1, wherein oral and/or mucosal alterations due to inflammatory tissue induce the change.

14. A method of using a chewing gum according to claim 1 for the detection of inflammatory tissue in the mouth, wherein the chewing gum is chewed by the user until the change in the chewing gum is directly detectable by the user.

15. The chewing gum according to claim 1, wherein it is for identifying the presence of inflammatory tissues in the mouth in or adjacent to the mandible, the maxilla, an implant or the teeth of a user.

16. The chewing gum according to claim 1, wherein the marker inducing the change is a proteolytic enzyme released by macrophages.

17. The chewing gum according to claim 1, wherein the marker inducing the change is an activated matrix metalloproteinase.

18. The chewing gum according to claim 1, wherein the marker inducing the change is selected from the group consisting of: matrix metalloproteinase-8, activated matrix metalloproteinase-8, matrix metalloproteinase-2, activated matrix metalloproteinase-2, matrix metalloproteinase-9, activated matrix metalloproteinase-9 (aMMP-9), and a combination thereof.

19. The diagnostic chewing gum according to claim 1, wherein the element is a flavor molecule releasably covalently attached to the base material or to the particles embedded and/or attached to said base material.

20. The chewing gum according to claim 19, wherein the flavor molecule is attached to the base material or to the particles embedded and/or attached to said base material by means of a molecular chain cleavable under direct or indirect contact with the marker and wherein the molecular chain is a polypeptide chain of 3-7 amino acids, either directly or indirectly, via an anchoring element, attached to the base material or to the particles embedded or attached to said base material.

21. The chewing gum according to claim 3, wherein the flavor molecule upon release triggers the gustatory system of the user by stimulating a sweet and/or bitter taste.

22. The chewing gum according to claim 3, wherein the flavor molecule is a polypeptide chain of 3-7 amino acids, either directly or indirectly, via an anchoring element, attached to the base material.

23. The chewing gum according to claim 3, wherein the flavor molecule is a polypeptide chain with one of the sequences selected from the group consisting of SEQ-ID24-SEQ-ID44.

24. The chewing gum according to claim 1, wherein the change upon direct or indirect contact with the marker is triggered when a minimum marker concentration in saliva of the user is reached, wherein the marker is matrix metalloproteinase-8 or activated matrix metalloproteinase-8, and wherein the minimum marker concentration in saliva for the generation of a change in the chewing gum directly detectable by the user is above 1 ng/ml.

25. The chewing gum according to claim 1, wherein the change upon direct or indirect contact with the marker is triggered when a minimum marker concentration in saliva of the user is reached, and wherein the minimum marker concentration in saliva for the generation of a change in the chewing gum directly detectable by the user is above 5 ng/ml.

26. The chewing gum according to claim 1, wherein the change upon direct or indirect contact with the marker is triggered when a minimum marker concentration in saliva of the user is reached, and wherein the minimum marker concentration in saliva for the generation of a change in the chewing gum directly detectable by the user is above 8 ng/ml.

27. The chewing gum according to claim 1, wherein the change upon direct or indirect contact with the marker is triggered when a minimum marker concentration in saliva of the user is reached, wherein the marker is matrix metalloproteinase-8 or activated matrix metalloproteinase-8, and wherein the minimum marker concentration in saliva for the generation of a change in the chewing gum directly detectable by the user is in the range of 1-6000 ng/ml.

28. The chewing gum according to claim 1, wherein the change upon direct or indirect contact with the marker is triggered when a minimum marker concentration in saliva of the user is reached, wherein the marker is matrix is metalloproteinase-8 or activated matrix metalloproteinase-8, and wherein the minimum marker concentration in saliva for the generation of a change in the chewing gum directly detectable by the user is in the range of 5-4000 ng/ml.

29. The chewing gum according to claim 1, wherein the change upon direct or indirect contact with the marker is triggered when a minimum marker concentration in saliva of the user is reached, wherein the marker is matrix metalloproteinase-8 or activated matrix metalloproteinase-8, and wherein the minimum marker concentration in saliva for the generation of a change in the chewing gum directly detectable by the user is in the range of 8-2000 ng/ml.

30. The chewing gum according to claim 28, wherein the minimum marker concentration for the detection of peri-odontitis is a factor of 100 smaller than the minimum marker concentration for the detection of peri-implantitis, and wherein based on this critical concentration difference the generation of a change in the chewing gum directly detectable by the user is differentiated between periodontitis and peri-implantitis.

31. The chewing gum according to claim 28, wherein the minimum marker concentration for the detection of peri-odontitis is a factor of 500 smaller than the minimum marker concentration for the detection of peri-implantitis, and wherein based on this critical concentration difference the generation of a change in the chewing gum directly detectable by the user is differentiated between periodontitis and peri-implantitis.

32. The chewing gum according to claim 1, wherein the element is attached to a particle with a size in the range of 20-250 µm, wherein the particle is based on a polymer, copolymer, or a blend thereof.

33. The chewing gum according to claim 32, wherein the polymer or copolymer is selected from the group consisting of: polystyrene, poly(methylmethacrylate), polyethylene, polypropylene, poly(vinylchloride), polycarbonate, polyamide, polysulfone, poly(ethersulfone), polyether, poly(ether-ketone), poly(ether-ether-ketone), poly(tetrafluoroethylene), poly(vinylidenefluoride), polyester, poly(hydroxyalkanoate), polyurethane, polyimide, poly(etherimide), poly(butadiene), poly(vinylbutyral), polyanhydride, poly(amino acid), poly(organosiloxane), cellulose, chitin and a blend thereof.

34. The chewing gum according to claim 32, wherein the polymer or copolymer is selected from the group consisting of: polystyrene, poly(methylmethacrylate), polyethylene, polypropylene, poly(vinylchloride), polycarbonate, polyamide, polysulfone, poly(ethersulfone), polyether, poly(ether-ketone), poly(ether-ether-ketone), poly(tetrafluoroethylene), poly(vinylidenefluoride), polyester, poly(hydroxyalkanoate), polyurethane, polyimide, poly(etherimide), poly(butadiene), poly(vinylbutyral), polyanhydride, poly(amino acid), poly(organosiloxane), cellulose, chitin and a blend thereof,
and
wherein the element, is attached to the particle by means of coupling techniques selected from the group of coupling techniques consisting of: amide formation using peptide coupling; disulfide coupling; ester formation using carbodiimide-activated esterifications; urethane formation; urea formation; isothiourea formation, by reaction with diisocyanates or diisothiocyanates; ether formation, by reaction with epoxy group containing molecules, diepoxides, or with activated haloalkyl derivatives; reaction with dialdehydes followed by reductive amination; Michael-type addition reaction as performed by reaction of an acrylated reaction partner with a thiol-modified one; Click Chemistry coupling protocols, and by Cu(I)-promoted azide-alkyne [3+2] cycloaddition.

35. The chewing gum according to claim 1, wherein oral or mucosal alterations due to inflammatory tissue induce the change, selected from the group of at least one of the following inflammatory states: gingivitis, mucositis, periodontitis, and peri-implantitis.

36. Method of using a chewing gum according to claim 1 for the detection of inflammatory tissue in the mouth, in or adjacent to the mandible, the maxilla, an implant or the teeth of a user, wherein the chewing gum is chewed by the user until the change in the chewing gum is directly detectable by the user.

* * * * *

SEQUENCE LISTING

<160> NUMBER OF SEQ ID NOS: 46

<210> SEQ ID NO 1

```
<211> LENGTH: 8
<212> TYPE: PRT
<213> ORGANISM: Homo sapiens

<400> SEQUENCE: 1

Gly Pro Gln Gly Ile Ala Gly Gln
1               5

<210> SEQ ID NO 2
<211> LENGTH: 8
<212> TYPE: PRT
<213> ORGANISM: Homo sapiens

<400> SEQUENCE: 2

Gly Asn Gln Gly Ile Ala Gly Gln
1               5

<210> SEQ ID NO 3
<211> LENGTH: 8
<212> TYPE: PRT
<213> ORGANISM: Homo sapiens

<400> SEQUENCE: 3

Gly Leu Gln Gly Ile Ala Gly Gln
1               5

<210> SEQ ID NO 4
<211> LENGTH: 8
<212> TYPE: PRT
<213> ORGANISM: Homo sapiens

<400> SEQUENCE: 4

Gly Pro Asp Gly Ile Ala Gly Gln
1               5

<210> SEQ ID NO 5
<211> LENGTH: 8
<212> TYPE: PRT
<213> ORGANISM: Homo sapiens

<400> SEQUENCE: 5

Gly Pro Leu Gly Ile Ala Gly Gln
1               5

<210> SEQ ID NO 6
<211> LENGTH: 8
<212> TYPE: PRT
<213> ORGANISM: Homo sapiens

<400> SEQUENCE: 6

Gly Pro Gln Glu Ile Ala Gly Gln
1               5

<210> SEQ ID NO 7
<211> LENGTH: 8
<212> TYPE: PRT
<213> ORGANISM: Homo sapiens

<400> SEQUENCE: 7

Gly Pro Gln Phe Ile Ala Gly Gln
1               5

<210> SEQ ID NO 8
<211> LENGTH: 8
<212> TYPE: PRT
```

-continued

<213> ORGANISM: Homo sapiens

<400> SEQUENCE: 8

Gly Pro Gln Arg Ile Ala Gly Gln
1               5

<210> SEQ ID NO 9
<211> LENGTH: 8
<212> TYPE: PRT
<213> ORGANISM: Homo sapiens

<400> SEQUENCE: 9

Gly Pro Gln Gly Leu Ala Gly Gln
1               5

<210> SEQ ID NO 10
<211> LENGTH: 8
<212> TYPE: PRT
<213> ORGANISM: Homo sapiens

<400> SEQUENCE: 10

Gly Pro Gln Gly Tyr Ala Gly Gln
1               5

<210> SEQ ID NO 11
<211> LENGTH: 8
<212> TYPE: PRT
<213> ORGANISM: Homo sapiens

<400> SEQUENCE: 11

Gly Pro Gln Gly Ile Phe Gly Gln
1               5

<210> SEQ ID NO 12
<211> LENGTH: 8
<212> TYPE: PRT
<213> ORGANISM: Homo sapiens

<400> SEQUENCE: 12

Gly Pro Gln Gly Ile Glu Gly Gln
1               5

<210> SEQ ID NO 13
<211> LENGTH: 19
<212> TYPE: PRT
<213> ORGANISM: Homo sapiens

<400> SEQUENCE: 13

Ala Ser Gln Lys Arg Pro Ser Gln Arg His Gly Ser Lys Tyr Leu Ala
1               5                   10                  15

Thr Ala Ser

<210> SEQ ID NO 14
<211> LENGTH: 16
<212> TYPE: PRT
<213> ORGANISM: Homo sapiens

<400> SEQUENCE: 14

Ala Ser Gln Lys Arg Pro Gln Arg Ser Lys Tyr Leu Ala Thr Ala Ser
1               5                   10                  15

<210> SEQ ID NO 15
<211> LENGTH: 5
<212> TYPE: PRT

```
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(4)
<223> OTHER INFORMATION: Gly at position 3 and Leu at position 4 are
      linked by a (2-mercapto-4-methyl-pentanoyl) group
<220> FEATURE:
<221> NAME/KEY: MISC_FEATURE
<222> LOCATION: (5)..(5)
<223> OTHER INFORMATION: Amino acid has C-terminal OC2H5 group

<400> SEQUENCE: 15

Pro Leu Gly Leu Gly
1               5

<210> SEQ ID NO 16
<211> LENGTH: 4
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION

<400> SEQUENCE: 16

Gly Pro Leu Gly
1

<210> SEQ ID NO 17
<211> LENGTH: 3
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Amino acid has C-terminal -S-CH2CH(CH3)CH2CH3
      group

<400> SEQUENCE: 17

Pro Leu Gly
1

<210> SEQ ID NO 18
<211> LENGTH: 6
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: Amino acid has C-terminal OC2H5 group

<400> SEQUENCE: 18

Pro Leu Gly Leu Leu Gly
1               5

<210> SEQ ID NO 19
<211> LENGTH: 8
<212> TYPE: PRT
<213> ORGANISM: Homo sapiens
```

```
<220> FEATURE:
<221> NAME/KEY: MISC_FEATURE
<222> LOCATION: (1)..(1)
<223> OTHER INFORMATION: Pro is bound to dinitrophenyl
<220> FEATURE:
<221> NAME/KEY: MISC_FEATURE
<222> LOCATION: (8)..(8)
<223> OTHER INFORMATION: Xaa is D-Arg-OH

<400> SEQUENCE: 19

Pro Leu Gly Ile Ala Gly Gln Xaa
1               5

<210> SEQ ID NO 20
<211> LENGTH: 8
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Lys is bound to dinitrophenyl
<220> FEATURE:
<221> NAME/KEY: MOD_RES
<222> LOCATION: (8)..(8)
<223> OTHER INFORMATION: AMIDATION

<400> SEQUENCE: 20

Lys Pro Leu Gly Leu Lys Ala Arg
1               5

<210> SEQ ID NO 21
<211> LENGTH: 45
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is hydroxyproline
<220> FEATURE:
<221> NAME/KEY: MISC_FEATURE
<222> LOCATION: (6)..(6)
<223> OTHER INFORMATION: Xaa is hydroxyproline
<220> FEATURE:
<221> NAME/KEY: MISC_FEATURE
<222> LOCATION: (9)..(9)
<223> OTHER INFORMATION: Xaa is hydroxyproline
<220> FEATURE:
<221> NAME/KEY: MISC_FEATURE
<222> LOCATION: (12)..(12)
<223> OTHER INFORMATION: Xaa is hydroxyproline
<220> FEATURE:
<221> NAME/KEY: MISC_FEATURE
<222> LOCATION: (15)..(15)
<223> OTHER INFORMATION: Xaa is hydroxyproline
<220> FEATURE:
<221> NAME/KEY: MISC_FEATURE
<222> LOCATION: (27)..(27)
<223> OTHER INFORMATION: Lys is bound to dinitrophenyl
<220> FEATURE:
<221> NAME/KEY: MISC_FEATURE
<222> LOCATION: (33)..(33)
<223> OTHER INFORMATION: Xaa is hydroxyproline
<220> FEATURE:
<221> NAME/KEY: MISC_FEATURE
<222> LOCATION: (36)..(36)
<223> OTHER INFORMATION: Xaa is hydroxyproline
<220> FEATURE:
<221> NAME/KEY: MISC_FEATURE
<222> LOCATION: (39)..(39)
<223> OTHER INFORMATION: Xaa is hydroxyproline
<220> FEATURE:
<221> NAME/KEY: MISC_FEATURE
<222> LOCATION: (42)..(42)
<223> OTHER INFORMATION: Xaa is hydroxyproline
<220> FEATURE:
```

```
<221> NAME/KEY: MISC_FEATURE
<222> LOCATION: (45)..(45)
<223> OTHER INFORMATION: Xaa is hydroxyproline
<220> FEATURE:
<221> NAME/KEY: MOD_RES
<222> LOCATION: (45)..(45)
<223> OTHER INFORMATION: AMIDATION

<400> SEQUENCE: 21

Gly Pro Xaa Gly Pro Xaa Gly Pro Xaa Gly Pro Xaa Gly Pro Xaa Gly
1               5                   10                  15

Pro Lys Gly Pro Gln Gly Leu Arg Gly Gln Lys Gly Val Arg Gly Pro
            20                  25                  30

Xaa Gly Pro Xaa Gly Pro Xaa Gly Pro Xaa Gly Pro Xaa
        35                  40                  45

<210> SEQ ID NO 22
<211> LENGTH: 51
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is hydroxyproline
<220> FEATURE:
<221> NAME/KEY: MISC_FEATURE
<222> LOCATION: (6)..(6)
<223> OTHER INFORMATION: Xaa is hydroxyproline
<220> FEATURE:
<221> NAME/KEY: MISC_FEATURE
<222> LOCATION: (9)..(9)
<223> OTHER INFORMATION: Xaa is hydroxyproline
<220> FEATURE:
<221> NAME/KEY: MISC_FEATURE
<222> LOCATION: (12)..(12)
<223> OTHER INFORMATION: Xaa is hydroxyproline
<220> FEATURE:
<221> NAME/KEY: MISC_FEATURE
<222> LOCATION: (15)..(15)
<223> OTHER INFORMATION: Xaa is hydroxyproline
<220> FEATURE:
<221> NAME/KEY: MISC_FEATURE
<222> LOCATION: (33)..(33)
<223> OTHER INFORMATION: Lys is bound to dinitrophenyl
<220> FEATURE:
<221> NAME/KEY: MISC_FEATURE
<222> LOCATION: (39)..(39)
<223> OTHER INFORMATION: Xaa is hydroxyproline
<220> FEATURE:
<221> NAME/KEY: MISC_FEATURE
<222> LOCATION: (42)..(42)
<223> OTHER INFORMATION: Xaa is hydroxyproline
<220> FEATURE:
<221> NAME/KEY: MISC_FEATURE
<222> LOCATION: (45)..(45)
<223> OTHER INFORMATION: Xaa is hydroxyproline
<220> FEATURE:
<221> NAME/KEY: MISC_FEATURE
<222> LOCATION: (48)..(48)
<223> OTHER INFORMATION: Xaa is hydroxyproline
<220> FEATURE:
<221> NAME/KEY: MISC_FEATURE
<222> LOCATION: (51)..(51)
<223> OTHER INFORMATION: Xaa is hydroxyproline
<220> FEATURE:
<221> NAME/KEY: MOD_RES
<222> LOCATION: (51)..(51)
<223> OTHER INFORMATION: AMIDATION

<400> SEQUENCE: 22

Gly Pro Xaa Gly Pro Xaa Gly Pro Xaa Gly Pro Xaa Gly Pro Xaa Gly
1               5                   10                  15

Pro Ser Gly Ala Glu Gly Pro Lys Gly Pro Gln Gly Leu Arg Gly Gln
```

```
                    20                  25                  30

Lys Gly Val Arg Gly Pro Xaa Gly Pro Xaa Gly Pro Xaa Gly Pro Xaa
            35                  40                  45

Gly Pro Xaa
        50
```

<210> SEQ ID NO 23
<211> LENGTH: 48
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is hydroxyproline
<220> FEATURE:
<221> NAME/KEY: MISC_FEATURE
<222> LOCATION: (6)..(6)
<223> OTHER INFORMATION: Xaa is hydroxyproline
<220> FEATURE:
<221> NAME/KEY: MISC_FEATURE
<222> LOCATION: (9)..(9)
<223> OTHER INFORMATION: Xaa is hydroxyproline
<220> FEATURE:
<221> NAME/KEY: MISC_FEATURE
<222> LOCATION: (12)..(12)
<223> OTHER INFORMATION: Xaa is hydroxyproline
<220> FEATURE:
<221> NAME/KEY: MISC_FEATURE
<222> LOCATION: (24)..(24)
<223> OTHER INFORMATION: Lys is bound to dinitrophenyl
<220> FEATURE:
<221> NAME/KEY: MISC_FEATURE
<222> LOCATION: (30)..(30)
<223> OTHER INFORMATION: Xaa is hydroxyproline
<220> FEATURE:
<221> NAME/KEY: MISC_FEATURE
<222> LOCATION: (39)..(39)
<223> OTHER INFORMATION: Xaa is hydroxyproline
<220> FEATURE:
<221> NAME/KEY: MISC_FEATURE
<222> LOCATION: (42)..(42)
<223> OTHER INFORMATION: Xaa is hydroxyproline
<220> FEATURE:
<221> NAME/KEY: MISC_FEATURE
<222> LOCATION: (45)..(45)
<223> OTHER INFORMATION: Xaa is hydroxyproline
<220> FEATURE:
<221> NAME/KEY: MOD_RES
<222> LOCATION: (48)..(48)
<223> OTHER INFORMATION: AMIDATION
<220> FEATURE:
<221> NAME/KEY: MISC_FEATURE
<222> LOCATION: (48)..(48)
<223> OTHER INFORMATION: Xaa is hydroxyproline

<400> SEQUENCE: 23

```
Gly Pro Xaa Gly Pro Xaa Gly Pro Xaa Gly Pro Xaa Gly Pro Lys Gly
1               5                   10                  15

Pro Gln Gly Leu Arg Gly Gln Lys Gly Val Arg Gly Leu Xaa Gly Gln
            20                  25                  30

Arg Gly Glu Arg Gly Pro Xaa Gly Pro Xaa Gly Pro Xaa Gly Pro Xaa
        35                  40                  45
```

<210> SEQ ID NO 24
<211> LENGTH: 12
<212> TYPE: PRT
<213> ORGANISM: Homo sapiens

<400> SEQUENCE: 24

```
Gly Thr Pro Gly Pro Gln Gly Ile Ala Gly Gln Arg
1               5                   10
```

```
<210> SEQ ID NO 25
<211> LENGTH: 13
<212> TYPE: PRT
<213> ORGANISM: Homo sapiens

<400> SEQUENCE: 25

Gly Thr Ala Gly Pro Pro Gly Thr Pro Gly Pro Gln Gly
1               5                   10

<210> SEQ ID NO 26
<211> LENGTH: 5
<212> TYPE: PRT
<213> ORGANISM: Homo sapiens

<400> SEQUENCE: 26

Ile Ala Met Glu Lys
1               5

<210> SEQ ID NO 27
<211> LENGTH: 6
<212> TYPE: PRT
<213> ORGANISM: Homo sapiens

<400> SEQUENCE: 27

Leu Leu Gly Ala Ile Leu
1               5

<210> SEQ ID NO 28
<211> LENGTH: 6
<212> TYPE: PRT
<213> ORGANISM: Homo sapiens

<400> SEQUENCE: 28

Ile Ala Gly Ile Phe Pro
1               5

<210> SEQ ID NO 29
<211> LENGTH: 4
<212> TYPE: PRT
<213> ORGANISM: Homo sapiens

<400> SEQUENCE: 29

Ile Ala Phe Pro
1

<210> SEQ ID NO 30
<211> LENGTH: 4
<212> TYPE: PRT
<213> ORGANISM: Homo sapiens

<400> SEQUENCE: 30

Ile Ala Gly Ile
1

<210> SEQ ID NO 31
<211> LENGTH: 4
<212> TYPE: PRT
<213> ORGANISM: Homo sapiens

<400> SEQUENCE: 31

Ile Phe Phe Pro
1
```

```
<210> SEQ ID NO 32
<211> LENGTH: 4
<212> TYPE: PRT
<213> ORGANISM: Homo sapiens

<400> SEQUENCE: 32

Ile Phe Ile Phe
1

<210> SEQ ID NO 33
<211> LENGTH: 4
<212> TYPE: PRT
<213> ORGANISM: Homo sapiens

<400> SEQUENCE: 33

Ile Phe Val Leu
1

<210> SEQ ID NO 34
<211> LENGTH: 4
<212> TYPE: PRT
<213> ORGANISM: Homo sapiens

<400> SEQUENCE: 34

Ile Phe Trp Ile
1

<210> SEQ ID NO 35
<211> LENGTH: 4
<212> TYPE: PRT
<213> ORGANISM: Homo sapiens

<400> SEQUENCE: 35

Ile Phe Trp Tyr
1

<210> SEQ ID NO 36
<211> LENGTH: 6
<212> TYPE: PRT
<213> ORGANISM: Homo sapiens

<400> SEQUENCE: 36

Tyr Ile Phe Pro Leu Val
1               5

<210> SEQ ID NO 37
<211> LENGTH: 4
<212> TYPE: PRT
<213> ORGANISM: Homo sapiens

<400> SEQUENCE: 37

Ile Trp Gly Gln
1

<210> SEQ ID NO 38
<211> LENGTH: 4
<212> TYPE: PRT
<213> ORGANISM: Homo sapiens

<400> SEQUENCE: 38

Ile Trp Ile Phe
1

<210> SEQ ID NO 39
<211> LENGTH: 4
```

```
<212> TYPE: PRT
<213> ORGANISM: Homo sapiens

<400> SEQUENCE: 39

Ile Trp Gly Pro
1

<210> SEQ ID NO 40
<211> LENGTH: 8
<212> TYPE: PRT
<213> ORGANISM: Homo sapiens

<400> SEQUENCE: 40

Ile Ala Gly Gln Ile Tyr Pro Ile
1               5

<210> SEQ ID NO 41
<211> LENGTH: 6
<212> TYPE: PRT
<213> ORGANISM: Homo sapiens

<400> SEQUENCE: 41

Ile Ser Pro Pro Pro Gly
1               5

<210> SEQ ID NO 42
<211> LENGTH: 7
<212> TYPE: PRT
<213> ORGANISM: Homo sapiens

<400> SEQUENCE: 42

Ile Ala Gly Gln Val Val Val
1               5

<210> SEQ ID NO 43
<211> LENGTH: 6
<212> TYPE: PRT
<213> ORGANISM: Homo sapiens

<400> SEQUENCE: 43

Gly Pro Phe Pro Val Ile
1               5

<210> SEQ ID NO 44
<211> LENGTH: 8
<212> TYPE: PRT
<213> ORGANISM: Homo sapiens

<400> SEQUENCE: 44

Phe Ala Leu Pro Glu Tyr Leu Lys
1               5

<210> SEQ ID NO 45
<211> LENGTH: 5
<212> TYPE: PRT
<213> ORGANISM: Homo sapiens

<400> SEQUENCE: 45

Leu Ile Tyr Pro Ile
1               5

<210> SEQ ID NO 46
<211> LENGTH: 4
<212> TYPE: PRT
<213> ORGANISM: Homo sapiens
```

```
<220> FEATURE:
<221> NAME/KEY: MISC_FEATURE
<222> LOCATION: (1)..(1)
<223> OTHER INFORMATION: Ethylated amino acid

<400> SEQUENCE: 46

Gly Pro Leu Gly
1
```